US00PP34185P2

(12) United States Plant Patent
Maillard

(10) Patent No.: US PP34,185 P2
(45) Date of Patent: May 3, 2022

(54) WHITE NECTARINE TREE NAMED 'NECTARSAFIR'

(50) Latin Name: ***Prunus persica* (L.) Batsch**
Varietal Denomination: NECTARSAFIR

(71) Applicant: AGRO SELECTIONS FRUITS, Elne (FR)

(72) Inventor: Arsène Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 17/300,851

(22) Filed: Nov. 29, 2021

(30) Foreign Application Priority Data

Nov. 30, 2020 (QZ) ..... PBR 2020/3064

(51) Int. Cl.
*A01H 6/74* (2018.01)
*A01H 5/08* (2018.01)

(52) U.S. Cl.
USPC ..... Plt./188

(58) Field of Classification Search
USPC ..... Plt./188
See application file for complete search history.

*Primary Examiner* — Annette H Para
(74) *Attorney, Agent, or Firm* — Birch, Stewart, Kolasch & Birch, LLP

(57) ABSTRACT

A new and distinct variety of white nectarine tree denominated 'NECTARSAFIR' which has fruits with high eating quality and very long shelf life without alteration before and after harvesting, with a semi-sweet white flesh at maturity time, and a red pigmentation into and around the stone cavity, and an attractive skin with a very high percentage of luminous purple red blush on skin surface, on a red background.

6 Drawing Sheets

Botanical classification: *Prunus persica* (L.) Batsch.

Variety denomination: 'NECTARSAFIR'.

This application claims priority of Community Plant Variety Right No. 2020/3064 filed on Nov. 30, 2020 (Nov. 30, 2020) which is hereby incorporated by reference in its entirety.

The new variety named 'NECTARSAFIR' is also known as 9C.02.250.16 NB or ASF17134. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'NECTARSAFIR', the provisional reference of this white nectarine tree variety was 9C.02.250.16, corresponding to the tree 250 located in line 02 of the parcel 9C and selected during the year 2016. The letters "NB" are related to the first letters of the type of tree in French (NB for "Nectarine Blanche", that means "white nectarine"). Once the hybrid selected, the breeder assigned a clone reference that begins with the letters "ASF" followed by the year of selection and a number corresponding to the maturity order. The final name is only assigned once the application, has been filed and the name approved after its publication in the official bulletin. For the variety 'NECTARSAFIR', the clone reference was 'ASF17134'.

BACKGROUND OF THE NEW VARIETY

The present invention relates to a new and distinct variety of white nectarine tree, *Prunus persica* (L.) Batsch, which has been given the variety denomination 'NECTARSAFIR'.

This new tree produces fruits with a long shelf life without alteration both on the tree after growth completion and after harvesting, very good eating quality, semi-clingstone white flesh fruits, generally with a red pigmentation around and into the stone cavity, for fresh market in August in the Pyrénées-Orientales department, France.

ORIGIN OF THE VARIETY

The 'NECTARSAFIR' white nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'NECTARSAFIR' variety results from controlled pollinated cross between the white nectarine variety named 'NECTARPERF' (U.S. Plant Pat. No. 23,357) which was used as the seed parent, or female parent, and the white flat nectarine variety named 'CAKEREDAL' (U.S. Plant Pat. No. 23,358) which was used as the pollen parent, or male parent.

The 'NECTARSAFIR' variety was obtained by hybridizing and propagated by grafting on a 'INRA® GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree, and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'NECTARSAFIR' white nectarine tree blooms during the first two weeks of March near Elne in the Pyrénées-Orientales department, France. The blooming period is considered medium. However, it was observed that its date of blooming seems to be highly dependant on climatic conditions.

The first fruit of 'NECTARSAFIR' ripens generally medium in the season, namely at the end of July or at the beginning of August. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
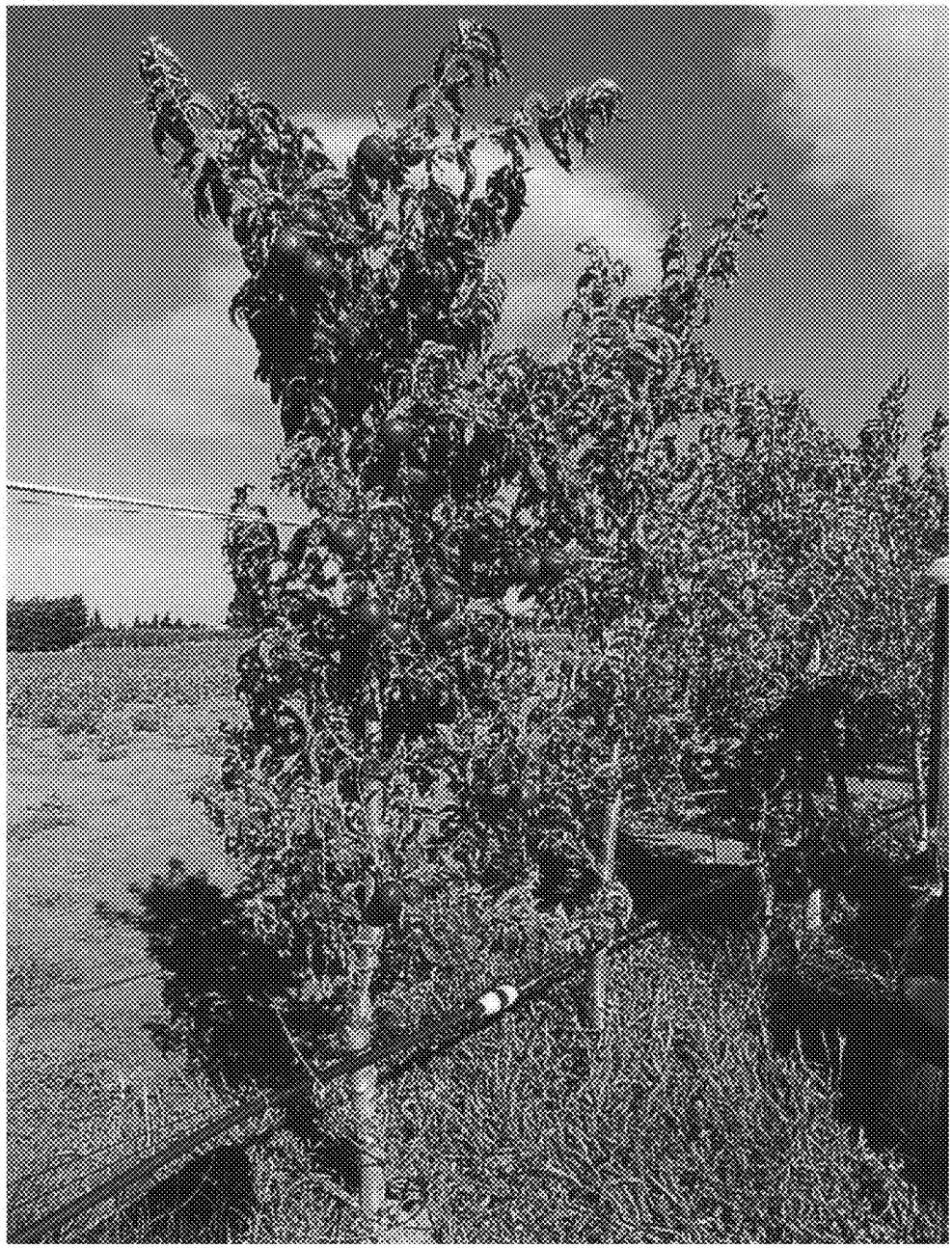
FIG. 1 is a color photograph showing a tree of the new variety 'NECTARSAFIR' in orchard, bearing fruits.
Figure 2:
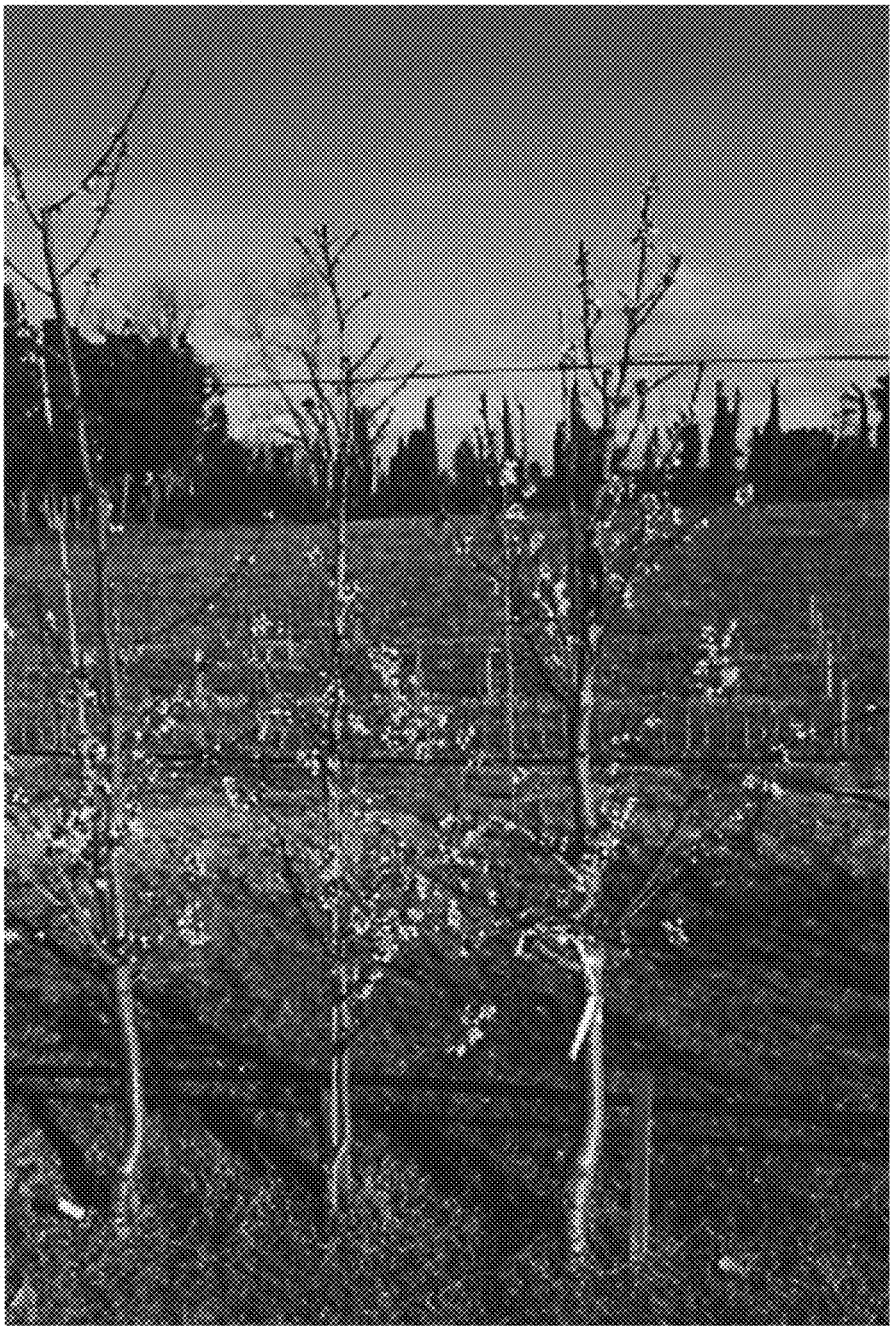
FIG. 2 is a color photograph showing three trees of the new variety 'NECTARSAFIR' in orchard, at blooming time.
Figure 3:
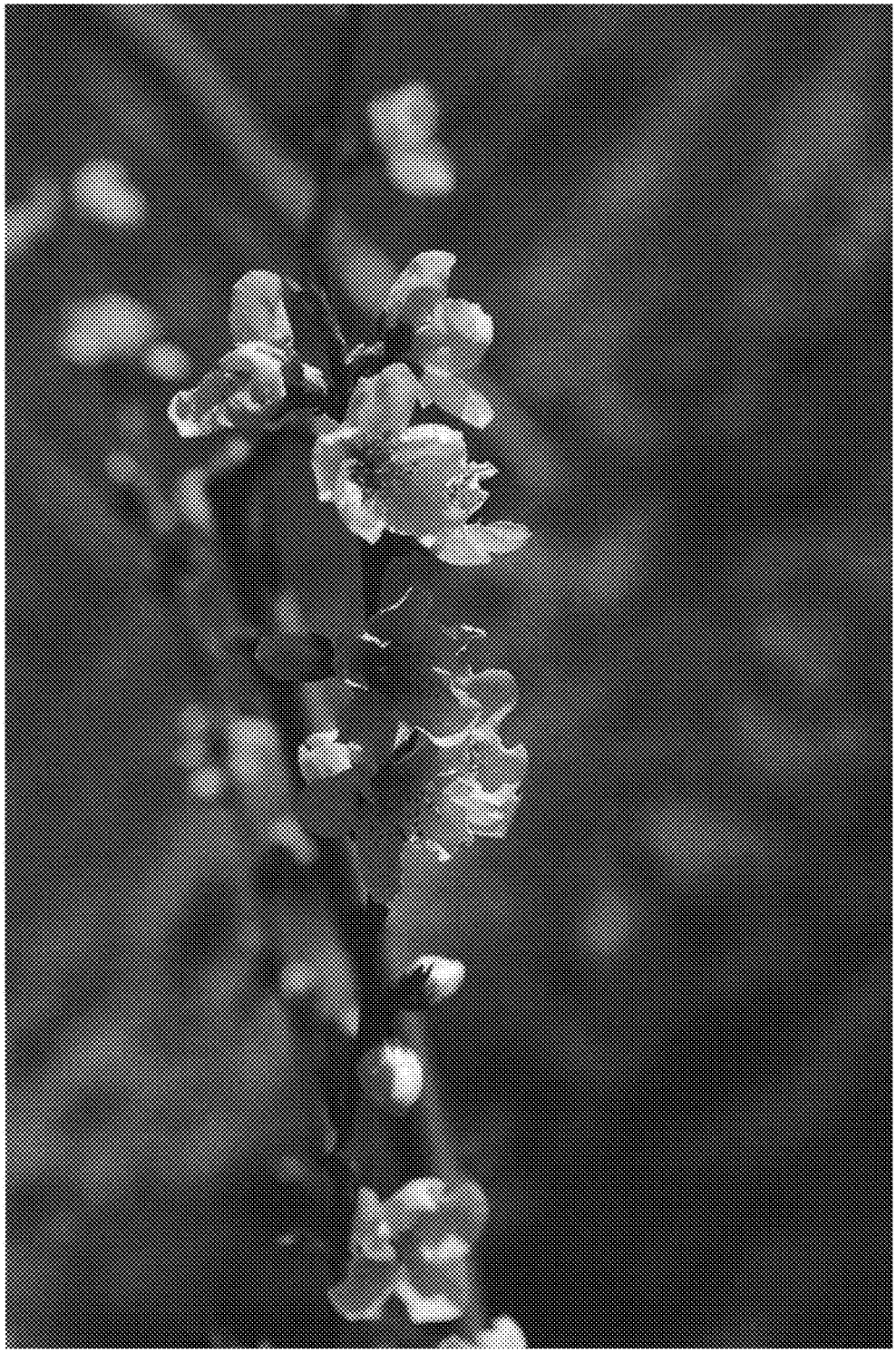
FIG. 3 is a color photograph showing a close view of a flowering branch of a tree of the new variety 'NECTARSAFIR' in orchard, at blooming time, some of the bunches of flowers being opened and some others being closed.
Figure 4:
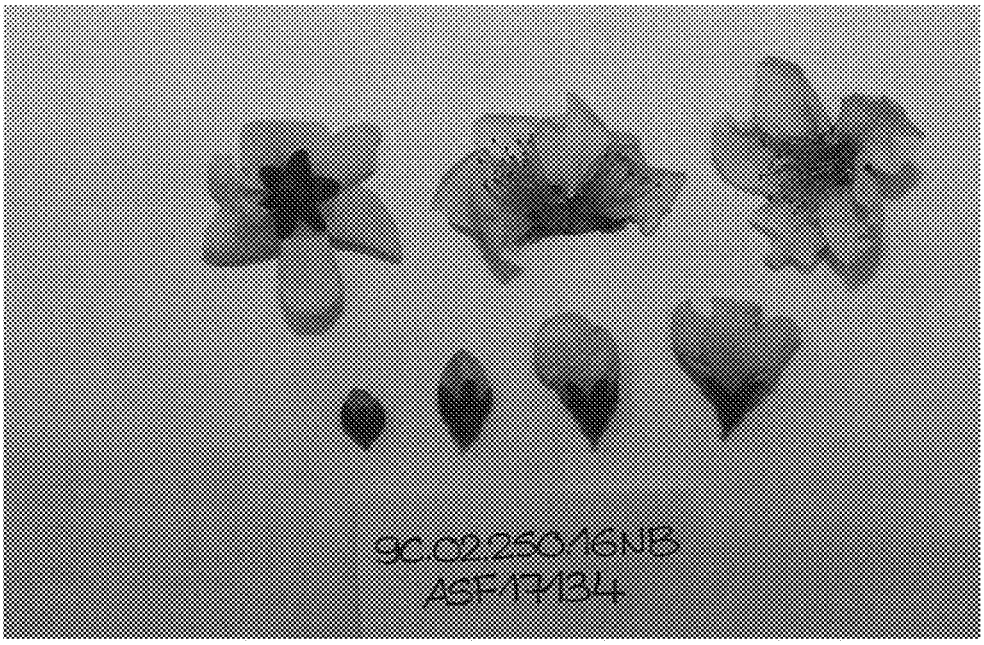
FIG. 4 is a color photograph which depicts the flower buds at different development stages, and the reverse and side views of the flower and the reproductive organs with petals removed, of the new variety 'NECTARSAFIR' also named '9C.02.250.16 NB ASF17134'.
Figure 5:
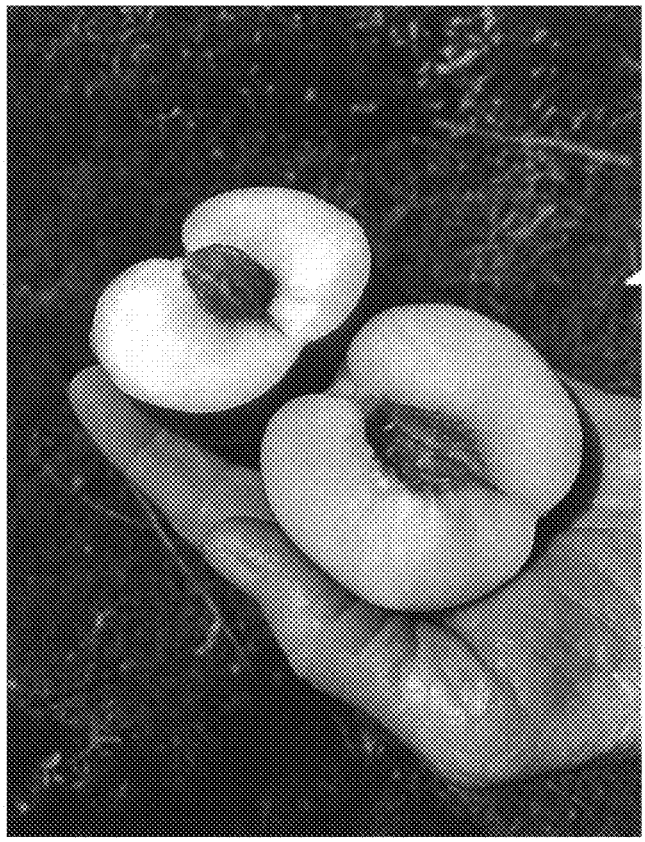
FIG. 5 is a color photograph which shows a close view of a fruit at maturity time, the fruit being cut in half with the pit being left in one of the halves.
Figure 6:
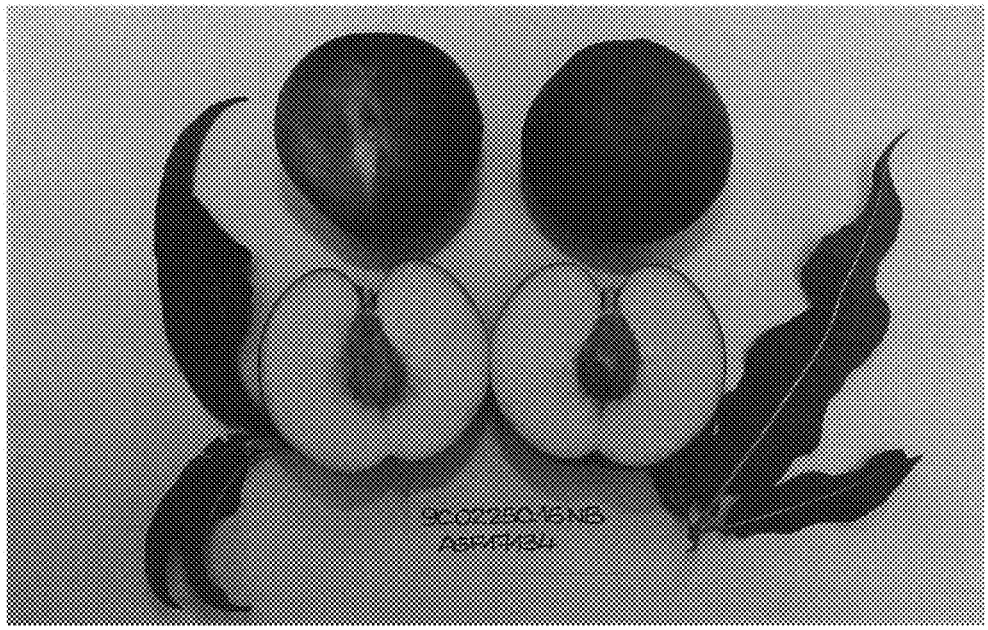
FIG. 6 is a color photograph which shows the upper and lower sides of leaves and different views of three typical specimens of the fruit of the new variety 'NECTARSAFIR' also named '9C.02.250.16 NB ASF17134' at ripening time, one fruit having been cut in half with the pit being left in one of the halves for depicting leaves, fruit flesh, pit and pit cavity of the new variety.
Figure 7:
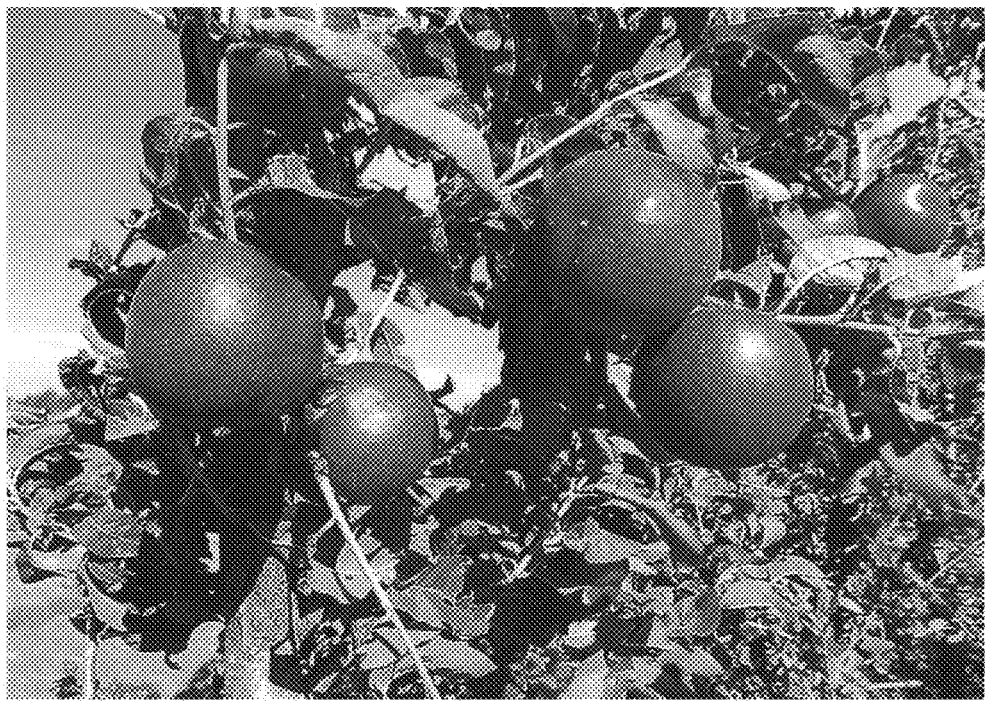
FIG. 7 is a color photograph showing a close view of some fruits of the new variety on tree in orchard, at ripening time.
Figure 8:
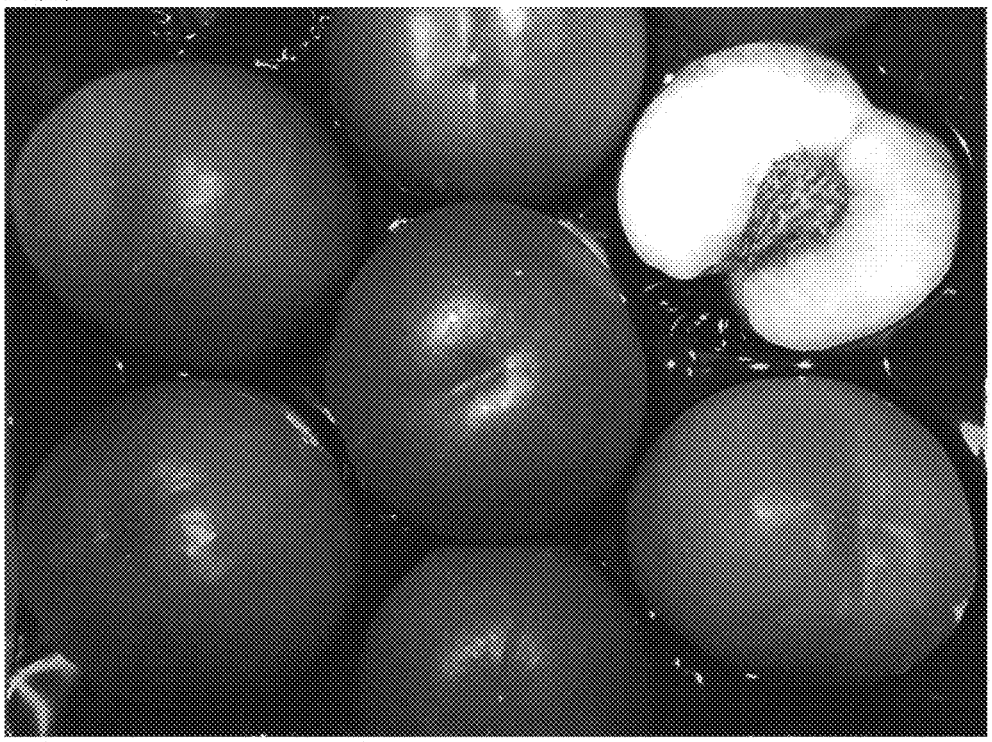
FIG. 8 is a color photograph that shows a close view of typical specimens of the fruits of the new variety at maturity time, one of these specimens being cut in half.

The views of trees, flowers, leaves and fruits have been photographed in their fourth growing season (third year of production).

Due to chemical development, processing and printing, the flowers, stones and fruits depicted in these photographs may or may not be accurate when compared to the actual botanical specimen.

DETAILED BOTANICAL DESCRIPTION

The trees, flowers, and fruits may vary in slight detail due to variations in soil type, cultural practices, and climatic condition. The potential for commercial production of fresh fruits by 'NECTARSAFIR' is high, due to fruit very long shelf life without alteration after harvesting.

Trees are medium vigorous and large stature half-standing in a semi-flared out aspect. The anthocyanic coloration of flowering shoot is present excluding brushwood side away from sun. The time of beginning of flowering is considered medium; flowering begins at the beginning of March. The type of flower is showy (rosette) with medium petal size. Petals are pink. Leaf glands are present and intermediate (round or reniform). The fruit flesh is white at complete maturity. The fruit flesh usually shows a red pigmentation into the stone cavity and radiating around the stone cavity. The fruit skin is medium thick, with a luminous purple red blush on a red background. The stone is semi-clingstone and its size is small. Fruit taste is semi-sweet, aromatic and with a high level of sugars.

Compared to 'NECTARDREAM' white nectarine variety (U.S. Plant Pat. No. 23,420), the fruits of 'NECTARSAFIR' usually ripen during the same period. However, the fruit skin of the new variety 'NECTARSAFIR' shows a luminous purple red color covering 90% of the skin surface, on a red or pink background, whereas the fruit skin color of the 'NECTARDREAM' white nectarine is less colored, namely with a garnet red color covering 60 to 90% of the skin surface. Moreover, the background of the skin of the 'NECTARDREAM' variety is considered green to cream green.

The fruit flesh of 'NECTARDREAM' is washed green whereas the fruit flesh of the new variety is white with a slightly pink coloration.

Compared to its seed or female parent, i.e., the 'NECTARPERF' (U.S. Plant Pat. No. 23,357) variety, the new variety 'NECTARSAFIR' has a later blooming period. Namely, the first flowers of 'NECTARSAFIR' bloom approximately 15 days later than the flowers of 'NECTARPERF'.

The first fruits of the new variety 'NECTARSAFIR' ripen one month earlier than the fruits of the variety 'NECTARPERF'.

The fruit skin of the new variety 'NECTARSAFIR' is more uniformly colored than the fruit skin of 'NECTARPERF'.

Compared to its pollen or male parent, i.e., the 'CAKEREDAL' (U.S. Plant Pat. No. 23,358) variety, the new variety NECTARSAFIR has a later blooming period. Namely, the first flowers of 'NECTARSAFIR' bloom approximately 15 days later than the flowers of 'CAKEREDAL'.

The first fruits of the new variety 'NECTARSAFIR' ripen one month later than the fruits of the variety 'CAKEREDAL'.

The fruit skin of the new variety 'NECTARSAFIR' is more uniformly colored than the fruit skin of 'CAKEREDAL'.

DETAILED DESCRIPTION

Referring more specifically to the pomological details of this new and distinct variety of white nectarine tree, the following was observed on trees in their fourth growing season (third year of production) under the ecological conditions prevailing at the orchards located near the town of Elne, Pyrénées-Orientales departement, France. All observations have been done on rootstock cultivars. Used rootstocks were 'INRA® GF677' (non-patented) trees. All major color code designations are by reference to The R.H.S. Colour Chart (Fourth Edition) provided by The Royal Horticultural Society of Great Britain.

Tree:

*Size.*—

*Generally.*—Considered large. The tree size the first year was approximately 200 to 280 cm. The tree was pruned during each following dormant season to a. height of approximately 250 cm. Current season shoots growth could reach 80 cm. The tree size from the second year (second and next years) reached a final height of 330 cm including current season shoots length. The tree size is consistently reduced to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered strong.

*Productivity.*—Considered good to very good, and very regular. Fruit set is spaced by thinning to develop the remaining fruit into the desired market sized fruit. The number of the fruit set varies with the prevailing climatic conditions and cultural practices employed during the bloom period and is therefore not distinctive of the present variety. A reduce vegetation, obtained with pruning or green pruning, approximately 1 month or 1 month ½ before harvesting fruits, significantly promotes fruit qualities, especially growth, color and firmness. Moreover, contamination risks due to *Monilia* or rot are significantly reduced. 'NECTARSAFIR' variety is not much sensitive to cracking of pistil cavity, to cork formation into peduncle cavity or to *Monilia.*

*Bearer.*—Very regular. The fruit distribution is considered homogenous on mixed branches and spurs having more than 1 year. Thinning of 2 fruits out of 3 was necessary for the tree valorisation. Thinning was necessary every year during the years of observation.

*Form.*—The 'NECTARSAFIR' variety has naturally a semi-flared shape.

*Density.*—Considered dense.

*Hardiness.*—Hardy in all stone fruit growing areas of France and especially where the chilling requirement is between 700 and 1200 hours. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017,1017 hours in 2017-2018, 844 hours in 2018-2019, 706 hours in 2019-2020 and 822 hours in 2020-2021 showed a good behavior of the tree in all cases. No injury with temperatures as low as −12° C. in winter. Good resistance to late frosts.

Trunk:

*Diameter.*—Approximately 65.0 to 72.0 millimeters in diameter when measured at a distance of approximately 20.0 centimeters above the soil level for trees on fourth leaf (or third year of production).

*Bark texture.*—Considered rough, with lenticels.

*Lenticels.*—Numerous lenticels are present. The number of lenticels reaches 2 lenticels per $cm^2$.The lenticels range in size of approximately 4.0 to 6.0 millimeters in width, and about 1.5 to 2.0 millimeters in height.

*Lenticel color.*—The lenticels show a beige color (RHS Greyed Orange 165 D).

*Bark coloration.*—The bark has a grey color (RHS Grey Green 197 A) darker than the lenticels color.

Branches:

*Size.*—The branches are pruned to approximately 1.0 meter in length.

*Diameter.*—Average as compared to other nectarine varieties. The current season shoots have a diameter of approximately 5.0 to 6.0 millimeters, and mature branches have a diameter of approximately 7.0 to 9.0 millimeters.

*Surface texture.*—Smooth for current season shoots and rough, with lenticels, for mature branches, wood which is several years old has no furrowed appearance.

*Crotch angles.*—Primary branches are considered variable, but the crotch angles are generally 45 degrees from the horizontal axis for current season shoots and 65° degrees from the horizontal axis for mature branches. This particular characteristic is not considered distinctive of the variety, however.

*Current season shoots.*—

*Internode length.*—Generally 22.0 to 28.0 millimeters.

*Color.*—The color of new shoot tips is considered light green (RHS Yellow Green 145 A) on lower part of new shoot tips, whereas the upper part is darker and colored in purple (RHS Greyed Red 183 A), depending on the level on the tip and the sunlight exposure.

*Mature branches.*—

*Internode length.*—Generally 26.0 to 32.0 millimeters.

*Color of mature branches.*—Brown (RHS Greyed Brown N 199 B or RHS Greyed Brown N 199 A).

*Lenticels.*—Numerous lenticels are present on mature branches. The number of lenticels reaches 3 lenticels per $cm^2$. The size of lenticels is considered small on one year's old shoots and medium on two-year-old shoots. The lenticel shape is stretched round with a diameter of approximately 1.0 to 1.5 millimeter on one-year-old shoots and a diameter between 1.5 and 2.0 on two-year-old shoots.

*Lenticel color.*—The lenticels on mature branches have a beige color (RHS Greyed Orange 165 C).

Leaves:

*Size.*—Considered medium for the species. The ratio leaf length/leaf width is 3.577.

*Leaf length.*—The medium length is about 130.20 millimeters with leaf petiole.

*Leaf width.*—The medium width is 36.40 millimeters.

*Leaf form (in cross section).*—Concave.

*Leaf form.*—Lanceolate.

*Leaf base shape.*—Round.

*Leaf tip form.*—Acute.

*Leaf thickness.*—Medium.

*Leaf color.*—

*Upper leaf surface.*—Yellow Green (RHS Yellow Green 147 A).

*Lower surface.*—A slightly lighter green (RHS Yellow Green 146 A) than the upper leaf surface color.

*Leaf texture.*—Smooth and glabrous on both upper and lower surfaces of the leaf.

*Leaf venation.*—Pinnately veined.

*Mid-vein.*—

*Color.*—Light green, almost cream white (RHS Yellow Green 145 A or RHS Yellow Green 145 B). The color may evolve with maturity.

*Width.*—Approximately 1.5 millimeters.

*Secondary veins.*—

*Color.*—Light green (RHS Yellow Green 145 C).

*Leaf margins.*—Slightly undulating.

*Form.*—Considered crenate.

*Uniformity.*—Leaves are isolated or grouped by 2 or 3. In this last case, one leaf of normal size is found with one or two smaller leaves (at least 50% smaller).

*Leaf petioles.*—

*Size.*—Considered small.

*Length.*—About 8.0 to. about 10.0 millimeters.

*Diameter.*—About 1.0 to 1.5 millimeters.

*Shape.*—Grooved.

*Petiole color.*—

*Upper petiole surface.*—Green (RHS Yellow Green 144 A or RHS Yellow Green 144 B).

*Lower surface.*—A slightly lighter green (RHS Yellow Green 144 C) than the upper petiole surface color.

*Leaf glands.*—

*Size.*—Considered medium. Their length is about 1.0 millimeter and their width is about 1.0 millimeter.

*Number.*—Generally 2 glands per leaf.

*Type.*—Intermediate, round or reniform.

*Margins.*—Smooth and regular.

*Position.*—Alternate on the upper part of petiole.

*Color.*—On young leaves, leaf glands color is considered a light green (RHS Yellow Green 145 A). On older leaves, leaf glands color turns to a brown (RHS Brown 200 A or RHS Brown 200 B) color.

*Leaf stipules.*—

*Generally.*—No leaf stipules were observed. But as seen in the characteristic relative to the leaves uniformity, it is possible to find leaves by groups of 2 or 3, with a normal-size leaf and smaller ones.

Flowers:

*Flower buds.*—

*Generally.*—At pre-floral stage of development, the floral buds are conic in shape. Their form is evolving until blooming, with variable dimensions. Just before blooming, floral buds are approximately 8.0 to 9.0 millimeters wide and approximately 10.0 to 12.0 millimeters long. The floral buds show a homogenous distribution on the trees.

*Color.*—This characteristic is dependent upon the proximity to bloom. At pre-floral stage of development, the bottom of the flower's buds, or calyx, or flower receptacle, is of purple color (RHS Greyed Purple 187 A or RHS Greyed Purple 187 B) on its outer face. The inner face of the flower receptacle is orange yellow (RHS Greyed Orange N163 B or RHS Greyed Orange N163 C). The corolla, formed by the petals, is generally of pink color (RHS Red Purple 65 A or RHS Red Purple 65 B) on both faces. Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins early in March. The first bloom was observed on Mar. 1, 2018.

*Blooming time.*—Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus, the full bloom was observed in 2018, from March $1^{st}$ until March $7^{th}$, then March $12^{th}$ until Mar. 16, 2019, then from March $3^{rd}$ to Mar. 8, 2020, and then from March $10^{th}$ to Mar. 15, 2021.

*Duration of bloom.*—Medium, approximately between 5 to 7 days. This characteristic varies slightly with the prevailing climatic conditions.

*Flower type.*—The variety is considered to have a showy type of flower.

*Flower size.*—Considered medium. Flower diameter at full bloom is approximately 33.0 to 36.0 millimeters.

*Bloom quantity.*—Considered high, approximately 55 flowers per meter, with a high rate of fruit set.

*Flower bud frequency.*—Generally 2 flower buds appear per node, occasionally 1.

*Petal size.*—

*Generally.*—Considered medium.

*Length.*—Generally between 16.0 and 17.0 millimeters.

*Width.*—Generally between 15.0 and 16.0 millimeters.

*Petal form.*—Round-shaped.

*Petal count.*—Sometimes more than 5.

*Petal arrangement.*—Overlapping.

*Petal texture.*—Smooth on both upper and lower surfaces of the petal.

*Petal color.*—At the stage F of blooming, when the flower is fully opened, both surfaces of the petal are colored with a pink (RHS Red Purple 65 B or RHS Red Purple 65 C) color when young, becoming slightly darker until the end of blooming.

*Fragrance.*—Slight to moderate.

*Petal claw.*—

*Form.*—The claw is considered to have a narrow form.

*Length.*—About 1.0 to 1.5 millimeters.

*Width.*—About 1.5 millimeters at the base.

*Color.*—The petal claw usually shows a pink color darker than the petal color (RHS Red Purple 60 B).

*Petal margins.*—Generally considered slightly undulating.

*Petal apex.*—

*Generally.*—The petal apices are generally shaped as a wide dome.

*Flower pedicel.*—

*Length.*—Considered medium and having an average length of approximately 2.5 to 3.0 millimeters.

*Diameter.*—Considered average, approximately 1.0 to 1.5 millimeters.

*Color.*—Green (RHS Yellow Green 144 A or RHS Yellow Green 144 B).

*Calyx.*—

*Internal surface texture.*—Smooth.

*Color.*—At the stage F of blooming, when the flower is opened, the inner surface of the calyx, namely the flower receptacle, is yellow orange (RHS Greyed Orange N163 B or RHS Greyed Orange N163 C). The outer surface of the calyx is considered of purple color (RHS Greyed Purple 187 A or RHS Greyed Purple 187 B).

*Sepals.*—

*Sepal count.*—Usually 5 sepals, sometimes 6.

*Surface texture.*—The outer surface has a short, fine pubescent texture.

*Margins.*—Smooth.

*Size.*—Medium.

*Length.*—Approximately 4.0 to 5.0 millimeters.

*Width.*—Approximately 4.0 to 5.0 millimeters.

*Form.*—Conic and round at the top.

*Color.*—The upper surface of the sepals shows a purple color (RHS Greyed Purple 187 A or RHS Greyed Purple 187 B) whereas the lower surface of sepals is considered greenish (RHS Grey Brown 199 A or RHS Grey Brown 199 B).

*Anthers.*—

*Generally.*—Medium in length.

*Shape.*—Cordate

*Color.*—Depending on the maturity stage, anthers are colored with a red (RHS Red 53 A) to a yellow color (RHS Yellow Orange 17C).

*Pollen production.*—Pollen is abundant and has a yellow color (RHS Yellow 13 A or RHS Yellow 13 B) which may evolve with maturity. The present variety is considered auto-fertile (self-pollinating).

*Pistil.*—

*Number.*—Usually 1.

*Generally.*—Average in size.

*Length.*—Approximately 13.0 to 15.0 millimeters including the ovary. Generally higher than filaments in length when considered without the ovary, or equal to filament length.

*Color.*—Considered green to light green (RHS Yellow Green N 144A or RHS Yellow Green 154 D) at the beginning of blooming period. The color evolves during the blooming to become yellow.

*Position.*—The pistil is positioned above the stamens.

*Ovary.*—

*Height.*—Approximately 1.5 to 2.0 millimeters.

*Diameter.*—Approximately 1.5 to 2.0 millimeters.

*Color.*—Green (RHS Yellow Green N 144C).

*Stamens.*—

*Size compared to petals.*—The size of stamen is smaller than the size of petals.

*Length.*—Approximately 12.0 to 14.0 millimeters, usually smaller than the pistil length and sometimes equal.

*Color.*—White (RHS White N 155 B) to pink (RHS Red Purple 62 B) depending on the maturity stage.

*Average number of stamens per flower.*—Approximately 35 to 40 stamens per flower.

*Stigma.*—

*Diameter.*—Approximately 0.75 millimeter.

*Color.*—Greenish yellow (RHS yellow Green 151 B).

Fruit:

*Maturity when described.*—Firm in ripe conditions (shipping ripe).

*Date of first picking.*—Jul. 28, 2018.

*Date of last picking.*—The date of harvest varies slightly with the prevailing climatic conditions. The 'NECTARSAFIR' variety has a mid-season date of picking, and a grouped maturity. The maturity is grouped within 9 days and the harvest is generally performed in two runs. Last known picking times carry on from July 28$^{th}$ to Aug. 5, 2018, August 8$^{th}$ to Aug. 16, 2019, then from July 30$^{th}$ to Aug. 7, 2020, and then from August 6$^{th}$ to Aug. 14, 2021.

*Size.*—

*Generally.*—Homogeneous in size, size A to 2A. Considered medium.

*Average cheek diameter.*—Approximately 66.0 to 68.0 millimeters.

*Average axial diameter.*—Approximately 62.0 to 64.0 millimeters.

*Typical weight.*—Approximately 160.0 grams. This characteristic is high dependent upon the prevailing cultural practices, and therefore is not particularly distinctive of the variety.

*Fruit form.*—

*Generally.*—Round, regular and symmetrical. The fruit is generally uniform in symmetry, viewed from the suture's plane.

*Suture.*—

*Fruit suture.*—The suture is usually absent, or wide-mouthed and slightly marked when present, extending from the base to the apex. No apparent callousing or stitching exists along the suture line. Not pointed.

*Ventral surface.*—

*Form.*—Smooth.

*Apex.*—Slightly depressed.

*Mucron.*—Absent.

*Closing of the pistil cavity.*—Very good. The pistil cavity is not visible.

*Stem cavity.*—Average depth of the stem cavity is considered medium, about 12.0 to 14.0 millimeters. Average width is between 19.0 and 20.0 millimeters, and the stem cavity is flared.

*Fruit skin.*—

*Thickness.*—Considered medium and strong, and the skin adherence to flesh is medium.

*Texture.*—The pubescence of the skin is absent. The fruit skin is smooth.

*Taste.*—Semi-sweet, sugary.

*Tendency to crack.*—None observed.

*Color.*—

*Blush color.*—This blush color is a solid luminous purple red (RHS Greyed Purple 187 A). The purple red blush covers approximately 90% of the fruit skin surface on a red background (RHS Orange Red N34 A) on approximately 10% of the fruit skin surface. The percentage of the blush on the fruit skin surface can vary and is generally dependent upon the prevailing conditions under which the fruit was grown.

*Ground color.*—The ground color covers approximately 10% of the fruit skin surface, and is considered red (RHS Orange Red N34 A).

*Lenticels.*—A few lenticels are present.

*Fruit stem.*—Medium in length, approximately 7.0 to 9.0 millimeters.

*Diameter.*—Approximately 4.0 to 5.0 millimeters.

*Color*.—Pale green (RHS Yellow Green 145 A).

*Flesh*.—

*Ripens*.—Very homogenously, slowly. The flesh has a long shelf life.

*Texture*.—Firm, crunchy, melting, juicy at harvest maturity stage.

*Fibers*.—Not fibrous.

*Aroma*.—Considered present.

*Eating quality*.—Considered good, sugary and aromatic.

*Flavor*.—Considered semi-sweet. The Brix is generally superior to 13, with an average value at 13.3, and acidity is very low.

*Juice*.—Juicy at complete maturity. The juice shows a cream color.

*Brix*.—Generally between 12.8 and 14.0 degrees. The medium Brix is 13.3 degrees. This characteristic varies slightly with the number of fruits per tree, prevailing cultural practices and the surrounding climatic conditions.

*Flesh color*.—The flesh is considered white (RHS White 155 A) and becomes pink at complete maturity, usually with a red pigmentation (RHS Red 47 A) into the stone cavity and radiating around the stone cavity on approximately 3.0 to 4.0 millimeters.

Stone:

*Type*.—Semi-Clingstone, more or less semi-adherent depending on the fruit maturity.

*Size*.—Considered small for the variety. The stone size varies significantly depending upon the tree vigor, crop load and prevailing growing conditions.

*Length*.—Approximately 25.0 millimeters.

*Width*.—Approximately 20.0 millimeters.

*Diameter*.—Approximately 16.0 millimeters.

*Form*.—Elliptical.

*Base*.—Round.

*Apex*.—

*Shape*.—The stone apex is short and pointed.

*Stone cavity*.—Considered small in size, with round form and dimensions corresponding to the stone's dimensions.

*Stone surface*.—

*Surface texture*.—The pit is transversely furrowed on its entire surface. Furrows are deeper and more oblate on lateral sides.

*Ridges*.—The surface texture is generally characterized by more prominent ridges along the ventral edges and at the apical tip.

*Ventral edge*.—

*Width*.—Narrow. Approximately 2.0 millimeters at mid-suture.

*Dorsal edge*.—

*Shape*.—Grooved.

*Stone color*.—The color of the dry stone is generally considered light brown (RHS Greyed Orange 164 B or RHS Greyed Orange 164 C).

*Tendency to split*.—Splitting is absent.

*Kernel*.—

*Size*.—The kernel is considered small.

*Length*.—Approximately 12.0 millimeters.

*Width*.—Approximately 7.0 millimeters.

*Thickness*.—Approximately 5.0 millimeters.

*Form*.—Considered elliptical.

*Pellicle*.—The pellicle of the kernel has a short pubescence.

*Color*.—The kernel skin is brown colored (RHS Greyed Orange N167 A). The almond, which is the seed of the kernel, is white (RHS White 155 B) and has a sweet taste. The kernel and its embryo are mature at the time of fruit maturity.

*Use*.—The subject variety 'NECTARSAFIR' is considered to be a white nectarine tree having a medium season of maturity, and which produces fruits that are considered firm, attractively colored in purple red. Fruits have semi-sweet taste and are excellent for uncooked consumption, crunchy or melting when at full maturity. Fruits have excellent gustative qualities. Due to their flesh quality, firmness and density, they can also be commercialized as 4th range product (packed fruit or fruit in bags for example). And they are also useful for both local and very long-distance shipping.

*Keeping quality*.—Remarkable. Fruits have a slow maturation and a long shelf life both on the tree after growth completion and after harvesting without alteration. After growth completion, fruits are preserved more than one week. After harvest, fruits are well preserved more than 2 weeks at 2.0 degree Celsius.

*Shipping quality*.—Considered very good. The fruit of the new white nectarine variety showed minimal bruising of the flesh or skin damage after being subjected to normal harvesting and packing procedures. Its resistance to handling during harvest and packing and its long shelf life without alteration after harvest easily permit 2 weeks-shipping at 2 degrees Celsius.

*Resistance to insects and disease*.—No particular susceptibilities were noted. The present variety is not very sensitive to *Monilia* or rot. The pistil cavity is completely closed, generally without any cork formation.

Although the new variety of white nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of white nectarine tree as illustrated and described, characterized by fruits with high eating quality and very long shelf life without alteration before and after harvesting, with a semi-sweet white flesh at maturity time, and a red pigmentation into and around the stone cavity, and an attractive skin with a very high percentage of luminous purple red blush on skin surface, on a red background.

* * * * *